(12) United States Patent
Pacey (10) Patent No.: US 6,655,377 B2
(45) Date of Patent: Dec. 2, 2003

(54) INTUBATION INSTRUMENT

(75) Inventor: John A. Pacey, Vancouver (CA)

(73) Assignee: Saturn Biomedical Systems Inc., Burnaby (CA)

(*) Notice: Subject to any disclaimer, the term of this patent is extended or adjusted under 35 U.S.C. 154(b) by 0 days.

(21) Appl. No.: 10/356,705

(22) Filed: Jan. 30, 2003

(65) Prior Publication Data

US 2003/0168059 A1 Sep. 11, 2003

Related U.S. Application Data

(63) Continuation-in-part of application No. 09/732,129, filed on Dec. 6, 2000, now Pat. No. 6,543,447, which is a continuation-in-part of application No. 09/704,507, filed on Nov. 2, 2000, now abandoned, which is a continuation of application No. 09/060,891, filed on Apr. 15, 1998, now Pat. No. 6,142,144.

(60) Provisional application No. 60/352,283, filed on Jan. 30, 2002, provisional application No. 60/223,330, filed on Aug. 7, 2000, provisional application No. 60/168,711, filed on Dec. 6, 1999, provisional application No. 60/074,355, filed on Feb. 10, 1998, and provisional application No. 60/067,205, filed on Dec. 1, 1997.

(51) Int. Cl.[7] .......................... A61M 16/00; A61B 1/267
(52) U.S. Cl. ............................ 128/200.26; 128/207.14; 600/194
(58) Field of Search ..................... 128/200.24, 200.26, 128/204.17, 203.26, 203.27, 207.14, 207.15, 206.29, 911, 912, DIG. 26; 600/185, 186, 187, 188, 190, 194, 197, 199

(56) References Cited

U.S. PATENT DOCUMENTS

| 3,771,514 A | 11/1973 | Huffman |
| 4,114,609 A | 9/1978 | Moses |
| 4,126,127 A | 11/1978 | May |

(List continued on next page.)

FOREIGN PATENT DOCUMENTS

| WO | WO 98/41137 | 9/1998 |
| WO | WO 99/27840 | 6/1999 |

OTHER PUBLICATIONS

Flexible Laryngoscopes, 1 page specification sheet, Richard Wolf Gmbh, Circa Mar. 1997.

(List continued on next page.)

*Primary Examiner*—Weilun Lo
*Assistant Examiner*—Teena Mitchell
(74) *Attorney, Agent, or Firm*—Ipsolon LLP (57) ABSTRACT

The configuration and arrangement of the instrument greatly facilitate safe placement of the instrument and an associated endotracheal tube. The instrument includes a handle with an arm extending therefrom. The arm includes a base portion and a distal lifter portion preferably having an angle between 5° and 85°, inclusive, and the lifter is sized and shaped to engage or lift the patient's epiglottis, thereby to expose the glottis. In a preferred embodiment, the base portion and lifter portion are substantially the same length, and a viewing device, which is preferably a Charged Coupled Device ("CCD") or Complementary Metal Oxide Semiconductor ("CMOS") camera positioned near the transition portion between the base and lifter portions, is aligned to provide a perspective view toward the distal end of the lifter. Lights, which are preferably LED units, are positioned toward the distal end of the lifter to facilitate viewing. A heating element may be placed in thermal communication with the viewing device thereby defogging the viewing device during use. A transparent protective sheathing may be positioned over the assembly to facilitate cleaning and provide sterile multiple use of the device, and the lifter may be pivotally secured to the base portion to facilitate on-site adjustment by the practioner.

20 Claims, 8 Drawing Sheets

U.S. PATENT DOCUMENTS

| | | |
|---|---|---|
| 4,360,008 A | 11/1982 | Corazzelli, Jr. |
| 4,573,451 A | 3/1986 | Bauman |
| 4,592,343 A | 6/1986 | Upsher |
| 4,793,327 A | 12/1988 | Frankel |
| 4,832,004 A | 5/1989 | Heckele |
| 4,846,153 A | 7/1989 | Berci |
| 4,947,896 A | 8/1990 | Bartlett |
| 4,982,729 A | 1/1991 | Wu |
| 5,003,962 A | 4/1991 | Choi |
| 5,016,614 A | 5/1991 | MacAllister |
| 5,038,766 A | 8/1991 | Parker |
| 5,042,469 A | 8/1991 | Augustine |
| 5,095,888 A | 3/1992 | Hawley |
| 5,174,283 A | 12/1992 | Parker |
| 5,183,031 A | 2/1993 | Rossoff |
| 5,203,320 A | 4/1993 | Augustine |
| 5,261,392 A | 11/1993 | Wu |
| 5,329,940 A | 7/1994 | Adair |
| 5,339,805 A | 8/1994 | Parker |
| 5,381,787 A | 1/1995 | Bullard |
| 5,431,152 A | 7/1995 | Flam et al. |
| 5,443,058 A | 8/1995 | Ough |
| 5,498,231 A | 3/1996 | Franicevic |
| 5,513,627 A | 5/1996 | Flam |
| 5,551,946 A | 9/1996 | Bullard |
| 5,603,688 A | 2/1997 | Upsher |
| 5,645,519 A | 7/1997 | Lee et al. |
| 5,665,052 A | 9/1997 | Bullard |
| 5,676,635 A | 10/1997 | Levin |
| 5,776,052 A * | 7/1998 | Callahan ..................... 600/194 |
| 5,800,344 A | 9/1998 | Wood, Sr. et al. |
| 5,827,178 A | 10/1998 | Berall |
| 6,142,144 A | 11/2000 | Pacey |
| 6,174,281 B1 * | 1/2001 | Abramowitz ............... 600/196 |
| 6,494,828 B1 * | 12/2002 | Berall ........................ 600/190 |
| 6,543,447 B2 * | 4/2003 | Pacey ................... 128/200.26 |

OTHER PUBLICATIONS

Adjustable Laryngo–pharyngoscope, 1 page specification sheet, Richard Wolf GmbH, Circa Apr. 1997.

* cited by examiner

INTUBATION INSTRUMENT

REFERENCE TO RELATED APPLICATIONS

This application is a continuation-in-part of U.S. patent application Ser. No. 09/732,129, filed on Dec. 6, 2000, and now allowed, U.S. Pat. No. 6,543,447, which was a continuation-in-part of U.S. patent application Ser. No. 09/704,507, filed on Nov. 2, 2000, now abandoned, which was a continuation of U.S. patent application Ser. No. 09/060,891, filed on Apr. 15, 1998, which issued as U.S. Pat. No. 6,142,144 on Nov. 7, 2000.

This application also claims priority to U.S. Provisional Application No. 60/352,283, filed on Jan. 30, 2002, U.S. Provisional Application No. 60/067,205, filed on Dec. 1, 1997, U.S. Provisional Application No. 60/074,355, filed on Feb. 10, 1998, U.S. Provisional Application No. 60/168,711 filed on Dec. 6, 1999, and U.S. Provisional Application No. 60/223,330, filed on Aug. 7, 2000.

FIELD OF THE INVENTION

This invention relates to endoscopic instruments, particularly to an intubation instrument, such as a laryngoscope.

BACKGROUND

Intubation of the human trachea is carried out daily in operating rooms and emergency facilities in order to facilitate respiration of a patient. The goal of the intubation process is to locate the distal end of an endotracheal tube in the larynx with the proximal end outside the patient's mouth.

Safe and effective intubation requires controlled insertion of the endotracheal tube through a patient's mouth so that the tube is directed to the upper part of the larynx, the glottis, without damaging or being blocked by the patient's tissue. To this end, intubation instruments have been developed. Such instruments generally provide a somewhat rigid structure that is inserted into the mouth of the patient so that the distal end of the instrument is located in the glottis, adjacent to the vocal cords. An endotracheal tube is slid through the instrument during or after insertion of the instrument.

Advanced intubation instruments provide a lighted telescope or fiber optic viewing device. The telescope is carried by the instrument with the objective lens located at the distal end of the instrument and arranged so that the user may, via the proximal, viewing end of the telescope, observe the advancement of the instrument and the endotracheal tube. Such instruments are normally referred to as laryngoscopes.

In designing such intubation instruments it is important to provide a configuration that permits quick location of the instrument and tube without injurious or fatal delay that may occur with repeated attempts.

Precisely locating an endotracheal tube is certainly critical. Facial and neck trauma or the presence of blood, excoriation, mucus etc. may cause misdirection of the tube into the patient's esophagus.

Common laryngoscopes offer an elongate, substantially straight blade portion having a distal end inserted through a patient's mouth as previously described. Examples of such devices may be found in U.S. Pat. No. 4,360,008 to Corazzelli, Jr. ("Corazzelli Jr."), and U.S. Pat. No. 5,827,178 to Berall ("Berall"). The geometry of these devices allow a practitioner to insert them while directly viewing the line of sight of the blade as it is inserted through a patient's mouth and travels to the glottis. However, the path from the patient's mouth to the glottis is not straight. Accordingly, during insertion of such laryngoscopes, the practitioner must physically manipulate a patient's head, usually by pulling the patient's head back to elevate the patient's chin, in an effort to provide as straight of a path for receiving the laryngoscope as possible. Such manipulation is undesirable, particularly where the patient may have an injured neck or head. Moreover, the practitioner's line of sight for inserting such straight devices is often blocked by interfering tissue and the like.

Inventor's have attempted to overcome these problems with known laryngoscopes by attempting to improve the practitioner's view during insertion. For example, Berall includes a camera mounted in the vicinity of the distal end of the blade and a viewer mounted to the laryngoscope, such that the practitioner has a simultaneous line of sight and camera view during insertion. However, such a camera view positioned toward the distal end is often unprotected from tissue and debris, and therefore becomes easily blocked. Moreover, such positioning is usually too close to offer the practitioner a helpful perspective to facilitate proper insertion and alignment of the laryngoscope and endotracheal tube within the larynx. Also, the straight blade remains difficult to properly insert.

Another attempted improvement to known laryngoscopes involves contouring the blade as shown in U.S. Pat. No. 5,800,344 to Wood ("Wood"), and slidably securing an image sensor along such a blade to facilitate viewing. However, to be properly inserted, such devices still require undesirable manipulation of a patient's head and neck.

To facilitate insertion of these types of known laryngoscopes, some inventors have added moving tips to the blades as shown in Corazzelli, Jr. However, these tips are generally too small to adequately support the epiglottis, and they still require the practioner to insert an elongate straight or substantially straight blade, thereby required undesirable manipulation of the patent's head and neck.

In addition, when cameras are inserted into a patient's pharynx, the cold lense of the cameras combined with the moisture and heat of the pharynx tend to form fog or condensation on the camera's lense, thereby rendering them useless. Efforts to prevent the fogging of these lenses during use have had limited success. For example, known defoggers include applying antifogging chemicals to the lenses of the cameras prior to insertion, or applying a spray of water onto the lense. These defogging options. can be time consuming and ineffective.

SUMMARY OF THE INVENTION

The present invention overcomes these and other problems of known intubation devices. It provides an intubation device that includes a configuration and arrangement of components that greatly facilitate rapid, safe placement of the instrument and associated endotracheal tube.

In accordance with one aspect of this invention, the instrument provides a blade or arm having an elongate base portion and an elongate lifter portion having a distal end thereof extending therefrom, preferably at an angle between 15° to 85°, inclusive. The lifter is sized and shaped to engage, lift and support the patient's epiglottis, thereby to expose the glottis.

In a preferred embodiment, the base portion and lifter portion are substantially the same length, and a viewing device, which is preferably a Charged Coupled Device ("CCD") or Complementary Metal Oxide Semiconductor ("CMOS") camera positioned near the transition portion between the base and lifter portions, is aligned to provide a perspective view toward the distal end of the lifter. Lights, which are preferably Light Emitting Diode ("LED") units, are positioned toward the distal end of the lifter to facilitate viewing. A transparent protective sheathing may be positioned over the assembly to facilitate cleaning and provide sterile multiple use of the device.

In an alternative embodiment, the lifter is pivotally secured to the base portion such that the optimal angle for a particular patient may be selected on site by the practitioner.

The instrument can also provide a path for guiding movement of the endotracheal tube in a manner that permits the distal end of the tube to move along the instrument directly toward the glottis. In such case, the instrument includes a passage into which a telescope is mounted. The arrangement of the guide path and passage ensures that the distal end of the tube remains observable as it is advanced to the glottis.

The observation of the movement of the instrument and tube is enhanced by the creation of a clearing at the distal end of the instrument. In this regard, the instrument includes structure for establishing a clearing at the distal end of the instrument, into which clearing the patient's tissue is prevented from entering. The inner end of the viewing device is located at this clearing, as well as advantageously placed suction tube(s) for ensuring that the clearing remains free of fluid and vapor that would otherwise obstruct the operator's view.

Moreover, a projecting guard is included for establishing the clearing. The guard is angled in a manner that permits smooth, sliding movement of the instrument across tissue to the desired, inserted position of the instrument.

In preferred embodiments of the invention, the instrument may include a second fluid passageway for delivering fluid to or from the distal end of the instrument. Moreover, the instrument can be configured to provide a channel for guiding secondary instruments, such as forceps, for clearly observed removal of foreign material in the larynx.

Also, a defogging element assembly may be operably secured to the instrument. The defogging element includes a heating element thermally-coupled to the lense of the viewer. The heating element heats when needed thereby warming the lense and preventing condensation or fog from forming on the lense.

Other advantages and features of the present invention will become clear upon study of the following portion of this specification and drawings.

DETAILED DESCRIPTION OF PREFERRED EMBODIMENTS

Figure 9:
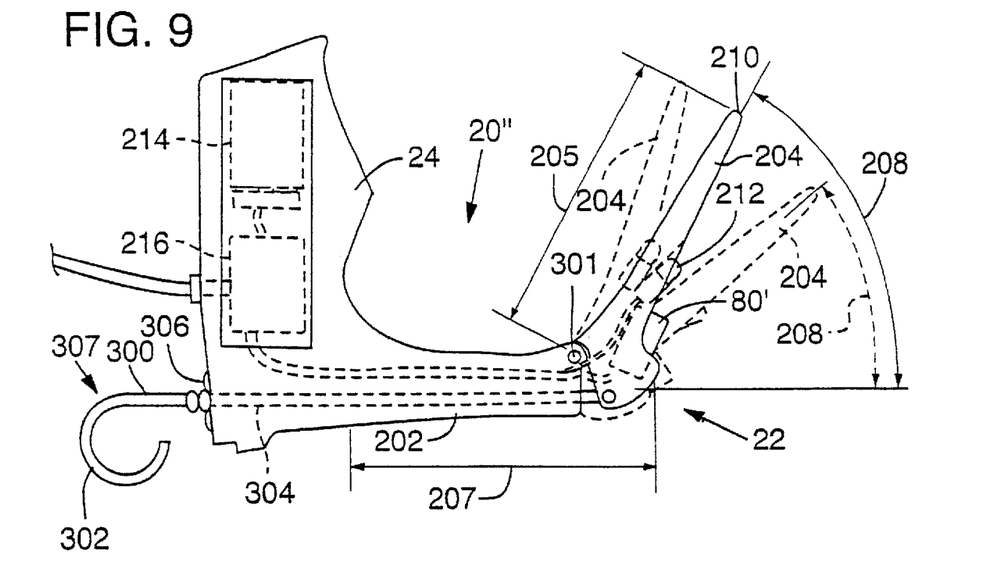
FIG. 9 is a side, elevation view of a third alternative preferred embodiment of an instrument made in accordance with the invention.
Figure 10:
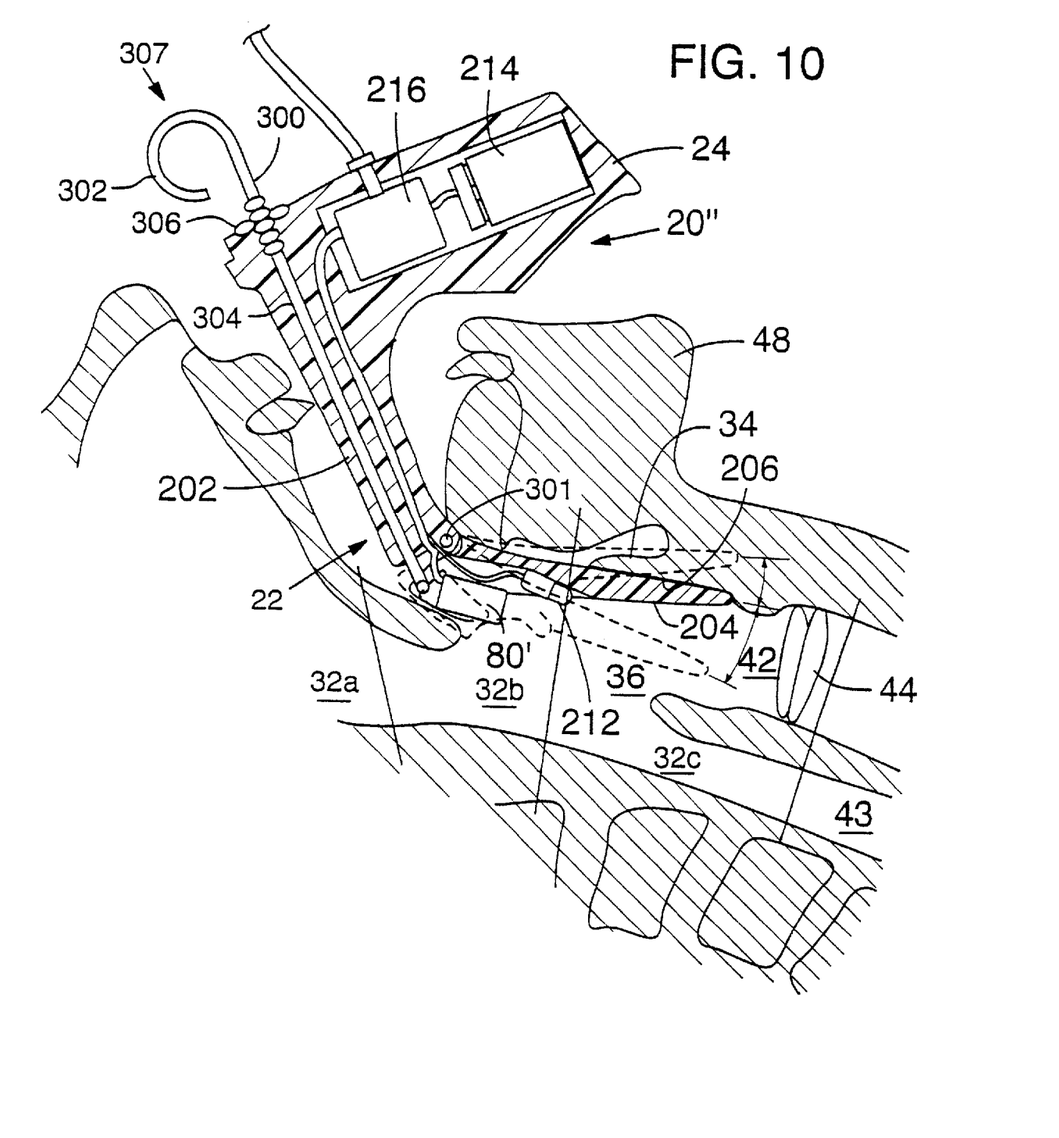
FIG. 10 is a side, elevation view of the instrument of FIG. 9 shown inserted into the mouth of a patient.

An improved intubation instrument in accordance with preferred embodiments of the present invention is shown in FIGS. 1–13. In particular, FIGS. 1–6 show a first preferred embodiment, FIGS. 7, 8 and 11A–B show a second preferred embodiment, and FIGS. 9 and 10 show a third preferred embodiment. In order to avoid unnecessary repletion, common elements between these three embodiments are like numbered.

A. First Preferred Embodiment

Figures 1, 5:
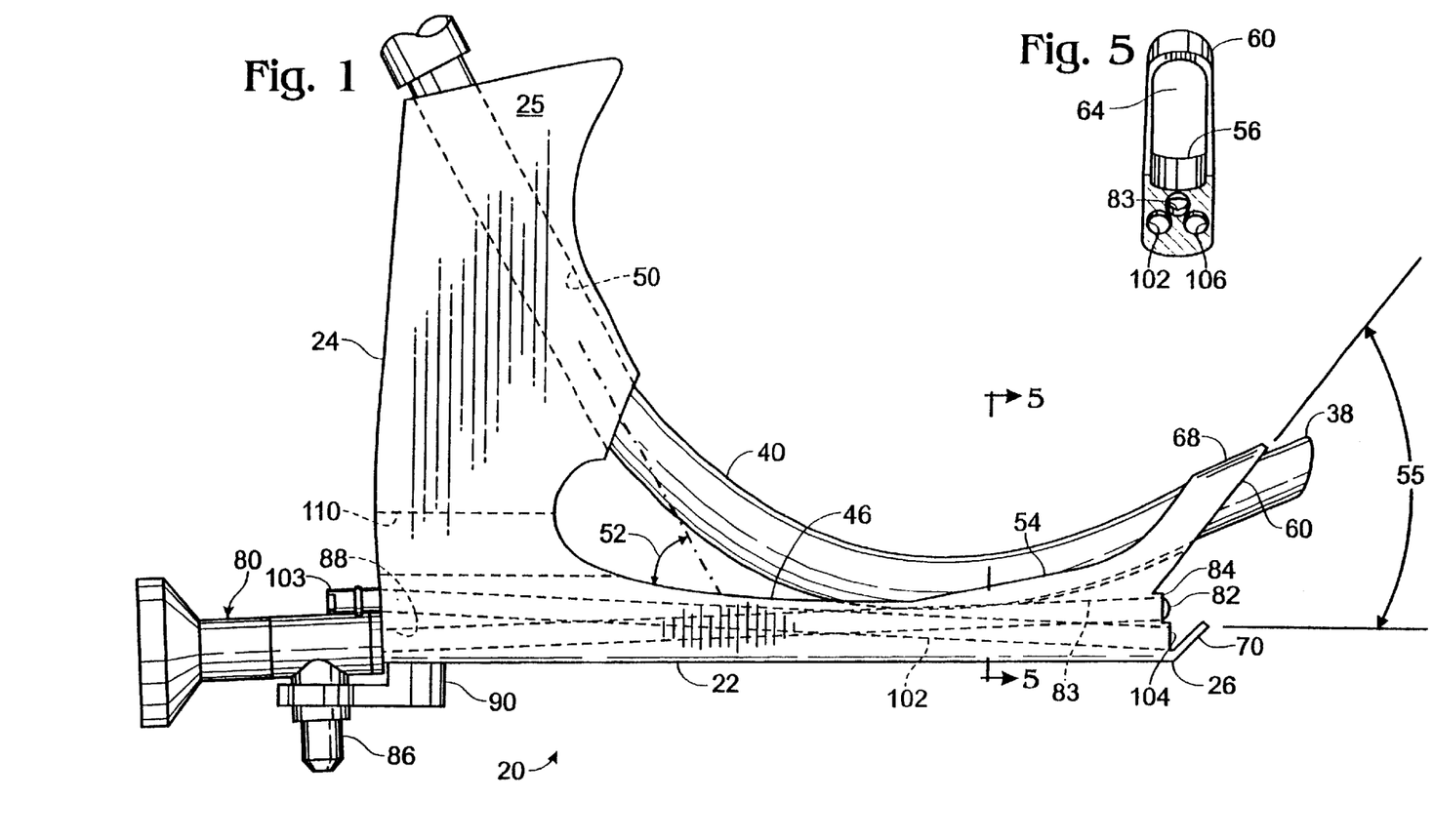
FIG. 1 is a side, elevation view of a preferred embodiment of an instrument made in accordance with the invention shown carrying an endotracheal tube.
FIG. 5 is a cross section taken about line 5—5 of FIG. 1.
Figure 6:
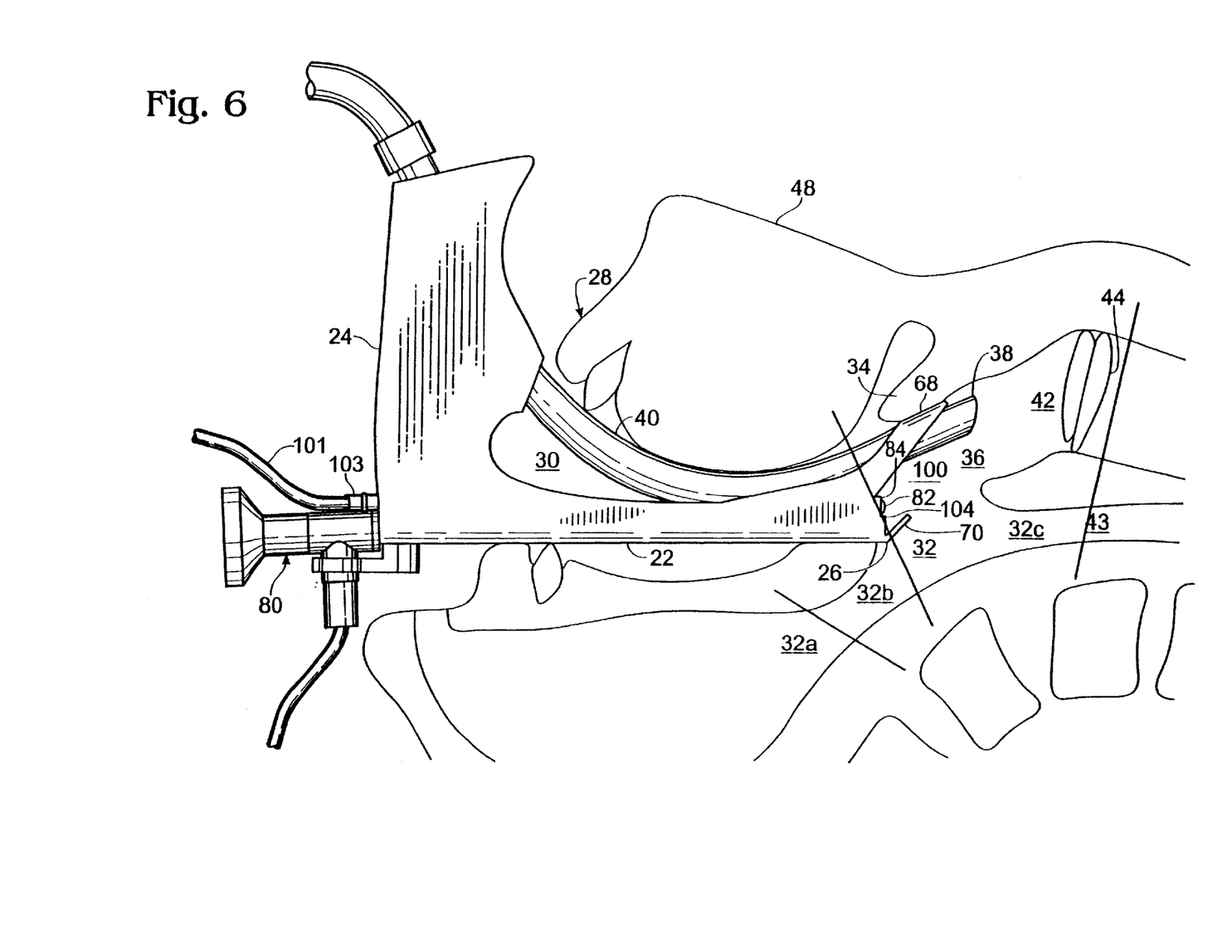
FIG. 6 is a side view of the instrument of FIG. 1 shown inserted into the mouth of a patient.

With particular reference to FIGS. 1 and 6, a first preferred embodiment of an intubation instrument made and used in accord with the present invention includes a body 20 that generally comprises an elongated arm 22 with integrally attached handle 24. The instrument is preferably formed from metal or rigid plastic that can withstand sterilization.

The instrument arm has a distal end 26 that is inserted into the mouth 30 of a patient 28. Preferably, the instrument is inserted while the patient is recumbent, face-up, with the head tipped slightly backwardly, supported in what is known as the sniffing position. Before proceeding with the description of the instrument, it will be useful here to identify the relevant components of the human patient (FIG. 6).

As noted, the instrument is inserted, distal end 26 first, through the patient's mouth 30. As explained below, when properly inserted, the distal end of the endotracheal tube 40 resides in the pharynx 32. Recently, individual portions of the pharynx 32 have become more commonly referred by those skilled in the art as the nasopharynx 32a (FIG. 6), the oropharynx 32b (FIG. 6), and the laryngopharynx 32c (FIG. 6). Accordingly, using these commonly known and more precise terms of the human respiratory system, the endotracheal tube 40 resides in the laryngopharynx 32c (FIG. 6). The patient's epiglottis 34 is supported by the instrument in a manner to expose the glottis 36. In the present invention, the instrument provides for the telescopically observed advance of the leading end 38 of an endotracheal tube 40 through the glottis 36, into the larynx 42 adjacent to the vocal cords 44. As is known in the art, an endotracheal tube 40 permits air to be conducted to and from an incapacitated patient. The present instrument includes a number of features that greatly increase the ease with which the instrument and tube 40 can be properly located and continuously observed via a telescope or other optic device.

More particularly, the arm 22 of the instrument is configured to define in the handle 24 and on its anterior surface 46 a guide path for the smooth advance of the tube 40 relative to the inserted instrument. For the purpose of this description, the anterior surface 46 of the instrument is, as shown in FIG. 6, that facing the lower jaw 48 of the intubated patient.

The guide path includes a portion consisting of a channel 50 (FIG. 1) that is formed through the handle 24. It is noteworthy that the handle 24 extends in a generally perpendicular orientation relative to the elongated arm 22. The channel 50, however, extends through the handle 24 at a direction that is generally oblique to the length of the handle 24 and to the arm 22. Put another way, the channel orientation 50 is such that after the leading end of the tube 40 is advanced through the channel 50, it emerges to contact the anterior surface 46 of the instrument at an acute angle 52 to slide along that surface toward the distal end 26 of the instrument.

Approaching the distal end of the instrument, the opposing anterior side edges 54 are gradually built up to define, in combination with the anterior surface part between the edges 54 a groove 56 that is generally curved in cross section, as best shown in FIG. 5. Preferably, the radius of curvature of the groove 56 generally conforms to the outside diameter of the tube 40. As such, the leading end of the tube 40 is precisely and smoothly guided through this groove 56, which makes up another part of the above mentioned guide path.

The side edges 54 terminate in a loop 60 that is part of the instrument and protrudes from the distal end 26 of the instrument at an angle 55 (FIG. 1) of about 45 degrees relative to the length of the arm 22. As viewed from the end (FIGS. 2 and 5), the loop defines an elongated opening 64 through which extends the leading end 38 of the tube 40.

Here it is useful to note that an endotracheal tube 40 used with the preferred embodiment of the instrument is formed of flexible plastic tubing. One such tube is that manufactured by Mallinckrodt, Inc. of St. Louis Mo., under the trademark Mallinckrodt. The tube is constructed to assume a curved configuration when relaxed, although it is readily deformed as needed. In the present invention, the loop 60 is configured to permit the leading end 38 of the tube 40 to approach its curved, relaxed configuration as it passes through and out of the loop 60.

Figure 2:
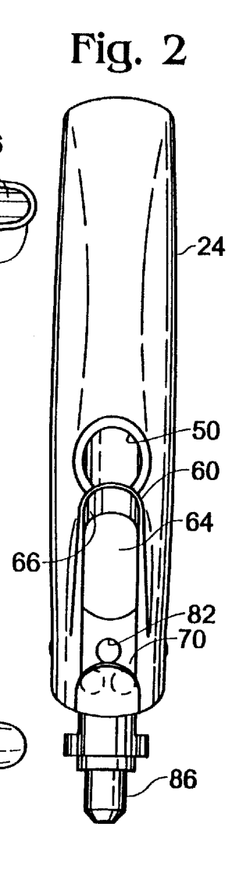
FIG. 2 is a front elevation view of the instrument shown in FIG. 1 with the endotracheal tube removed for clarity.
Figure 3:
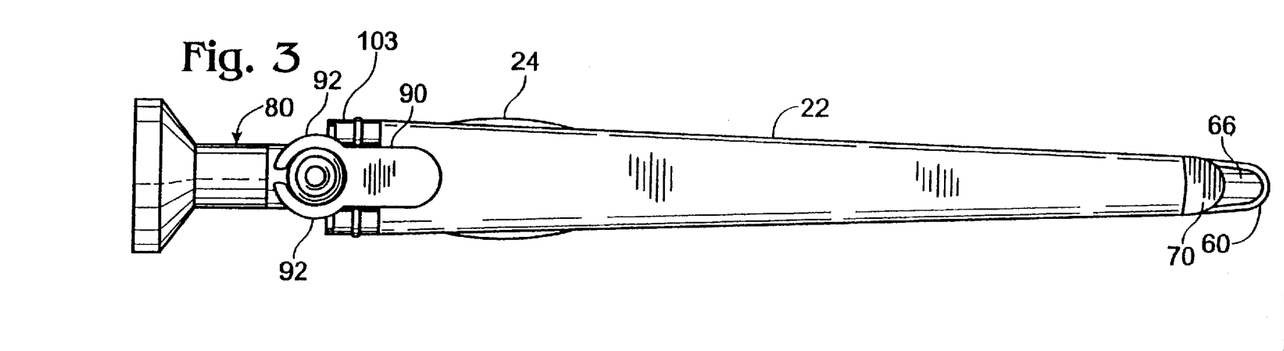
FIG. 3 is a bottom plan view of the instrument of FIG. 1
Figure 4:
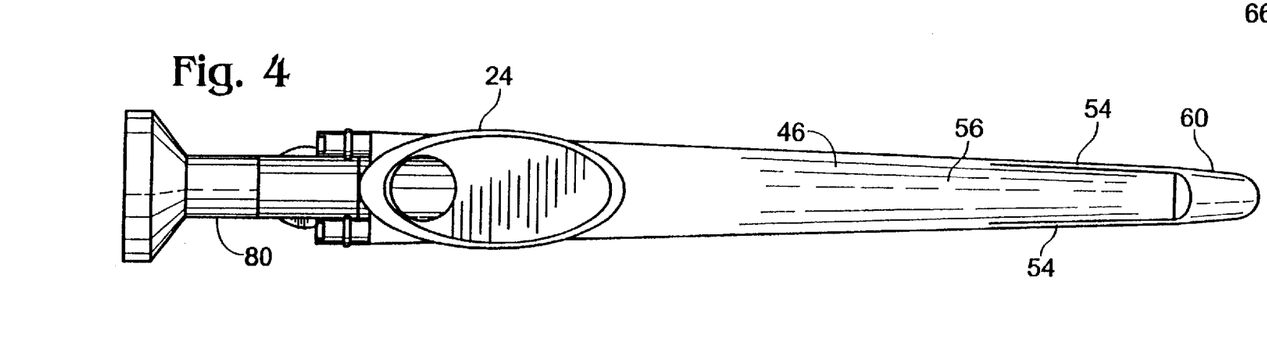
FIG. 4 is a top plan view of the instrument of FIG. 1.

More particularly, the elongated opening 64 (elongated, that is, in the direction away from the anterior surface of the arm 22, as shown in FIGS. 2 and 5) permits the flexible tube 40 to resile away from the distal end 26 of the arm 22 to seat against the underside 66 of the loop 60, as shown in FIG. 1. This underside 66 is curved to conform to the outside diameter of the tube, thereby providing, in a manner similar to the above-mentioned groove 56, precise and smooth guidance of the tube through the loop 60. Thus, the loop makes up another part of the above mentioned guide path. The advantages of the just described tube movement are discussed more fully below.

The loop 60 includes a surface 68 that bears against the patient's epiglottis 34 when the instrument is fully inserted. As a result, the epiglottis 34 and surrounding tissue are held by the instrument in a position where they do not occlude the glottis 36.

A guard 70 extends from the bottom of the instrument arm 22 at the distal end thereof. The guard is an extension of the arm 22 and is angled upwardly (as viewed in FIGS. 1 and 6) to present an underlying surface that acts like a skid upon insertion of the instrument to permit the distal end of the instrument to be advanced against the patient's tissue without damage to the tissue. Thus, the guard 70 reduces the effort needed to insert the device, while protecting the patient's tissue.

Once the arm 22 is in place, the guard 70 serves to prevent the tissue in the pharynx 32 from contacting the distal end 26 of the arm 22 and obstructing the view available to a viewer that is carried by the instrument. In this embodiment a telescope 80 is shown. In this regard, the telescope 80 is one that terminates in a long tubular member having an objective lens at its end 82. The terminus of the telescope fits into a telescope passage 83 that is formed through the arm 22. The telescope also includes a light post 86 that is mounted to the telescope 80 near the outer end 88 of the passage 83 and that provides illumination to the telescope 80. In a preferred embodiment of the instrument, a suitable telescope is one having approximately a 25-degree viewing angle; such as manufactured by Henke-Sass, Wolf of America Inc., Southbridge, Mass., as model number 8853.42.

In a preferred embodiment of the invention the instrument is provided with a clip 90 that is mounted to the arm 22 near the outer end of the passageway 83. The clip 90 includes two spaced-apart, arched arms 92 that spread apart slightly to releasably receive between them the generally cylindrical shaped light post 86 as the telescope is slid into position relative to the instrument 22. The clip 90, therefore, serves to retain the telescope in the correct location and within the telescope passage 83 during use. Moreover, since the arms 92 of the clip engage a radial projection of the telescope (namely, the light post 86), the telescope is held against inadvertent rotation out of the desired orientation relative to the arm 22. The arms 92 of the clip 90 are resilient and readily move apart to release the light post 86 when the telescope is pulled from the instrument for replacement and cleaning.

Returning to consider the distal end 26 of the arm 22, the end 82 of the telescope 80 is located at the inner end 84 of the passage 83 when the telescope is installed. As noted, the guard 70 prevents tissue from contacting the end of the telescope. More particularly, the telescope-guarding or tissue-retracting effect of both the loop 60 and the guard 70 has the effect of establishing a clearing 100 (FIG. 6), which is a space between the guard and loop, adjacent to the distal end of the instrument and free of view-obstructing tissue. The inner end 84 of the telescope passage (hence, the end 82 of an installed telescope) is in this clearing 100. Thus, the telescope is unaffected by tissue that would otherwise obstruct, at least in part, the telescopic view of the advancing, leading end 38 of the endotracheal tube 40.

As noted earlier, the loop 60 configuration is such that the tube that extends from the loop tends to assume its relaxed, curved shape. The leading end 38, therefore, tends to veer upwardly (considering FIG. 6) toward the glottis 36 and away from what would be a dangerous entry into the patient's esophagus 43.

The tube 40 is carried on the anterior surface 46 of the arm 22, between the patient's lower jaw and the telescope passage 83. This orientation, in combination with the curved guide path of the tube 40 ensure that the advancing, leading end 38 of the tube remains in the field of view of the telescope (as does the glottis) without crossing near the end 82 of the telescope, which crossing would obscure the view of the tube vis-a-vis the glottis 36.

For example, if the lens carried in the end 82 of the telescope is angled upwardly to provide a view in a direction toward the glottis 36, the movement of the tube end 38 out from beneath the underside of the loop 60 will be nearly parallel to a line defining the center of the field of view of the telescope. It has been found that this relative positioning of the telescope end 82 and tube end 38 greatly enhances viewing of the advancing tube as compared to instruments that went before.

The preciseness with which the present instrument may be inserted enables one to supply, during insertion, intermittent pulses of air (positive pressure) through the tube 40 to provide immediate respiration to the patient during the insertion process. Thus, the conventional air or oxygen supply to the tube may be so connected and controlled during insertion of the instrument.

The clearing 100 would be susceptible to entry of fluids such as blood, exudate, mucus etc, which might be present in instances of neck trauma. In accord with another aspect of this invention, there is provided efficient suction removal of such matter. To this end, the arm 22 is provided with a passageway 102 having an interior end 104 that opens at the distal end 26 of the instrument, below the inner end 84 of the telescope passage 83. A suction tube 101 (FIG. 6) may be attached to a connector 103 that is mounted to the instrument at the outer end of the passageway 102. Suction is applied for removing any fluid that may begin to accumulate in the clearing 100. It is noteworthy that the instrument is arranged so that the inner end of the telescope passage is above (FIG. 1) the interior end 104 of the suction passageway 102. Thus, the end 104 of the suction passageway resides in what may be called a sump portion of the clearing 100. Unwanted fluids are removed before reaching a level that would obscure the end 82 of an installed telescope 80.

It is contemplated that suction would be applied to the clearing 100 even in the absence of view-obstructing fluids because the application of suction would tend to cool the telescope (which is heated by the light source) or remove vapor that might otherwise tend to condense on the lens of the telescope.

Preferably, another passageway 106 (FIG. 5) is provided in the arm in a manner that substantially matches the suction passageway 102. This other passageway is available to hold another suction tube (thus enhancing overall suction of the clearing 100) or, alternatively, gas such as oxygen could be directed through this passageway 106 to increase the oxygen content of the glottis area.

The suction applied by one or both passages 102, 106 provides a vortex of fluid flow in the vicinity of the inner end 84 of the telescope passage, thereby providing a particularly effective way to remove from the telescope end (lens) 82 any fluid contamination, such as blood, that would otherwise obscure the view through the telescope. Thus, the telescope need not be removed for clearing the lens.

It will be appreciated that the arrangement of the various components of the instrument presents an instrument that is substantially symmetrical about the long axis of the arm and handle. Thus the instrument is readily useable by a right- or left-handed operator.

It is also contemplated that the channel 50 in the handle 24 may be configured to open on one side of the handle, such as surface 25 (FIG. 1) thereby forming the channel 50 as a groove in the handle. As a result, the tube 40 could be inserted laterally into the channel/groove. At the junction of the channel 50 and surface 25, the groove width could be narrowed somewhat, relative to the remainder of the groove, to a width just slightly narrower than the diameter of the flexible tube 40. Such a configuration permits the tube to be secured by a snapfit into this configuration of the channel.

B. Second Preferred Embodiment

Figure 7:
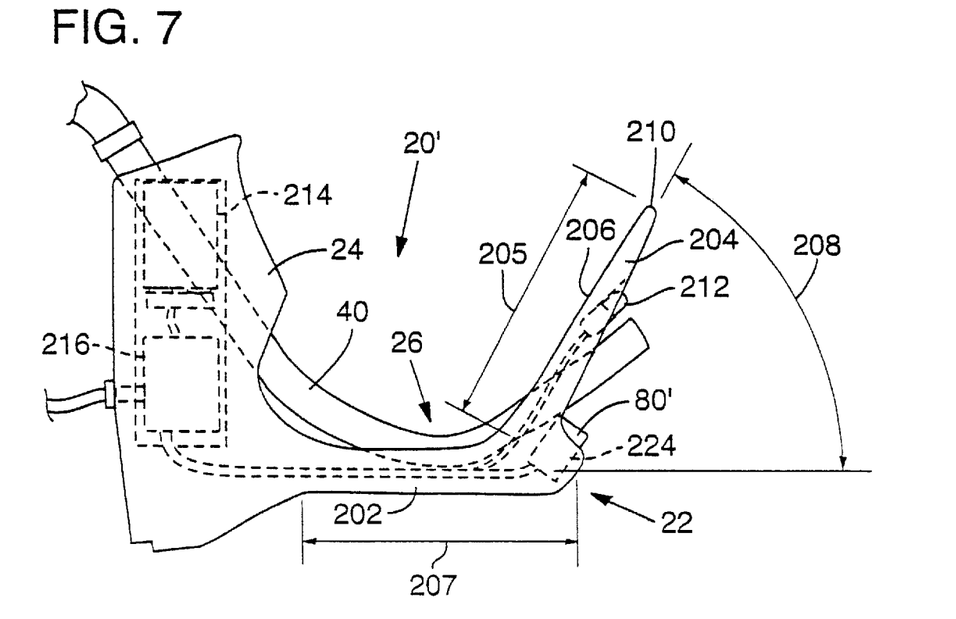
FIG. 7 is a side, elevation view of a second alternative preferred embodiment of an instrument made in accordance with the invention shown carrying an endotracheal tube.
Figure 8:
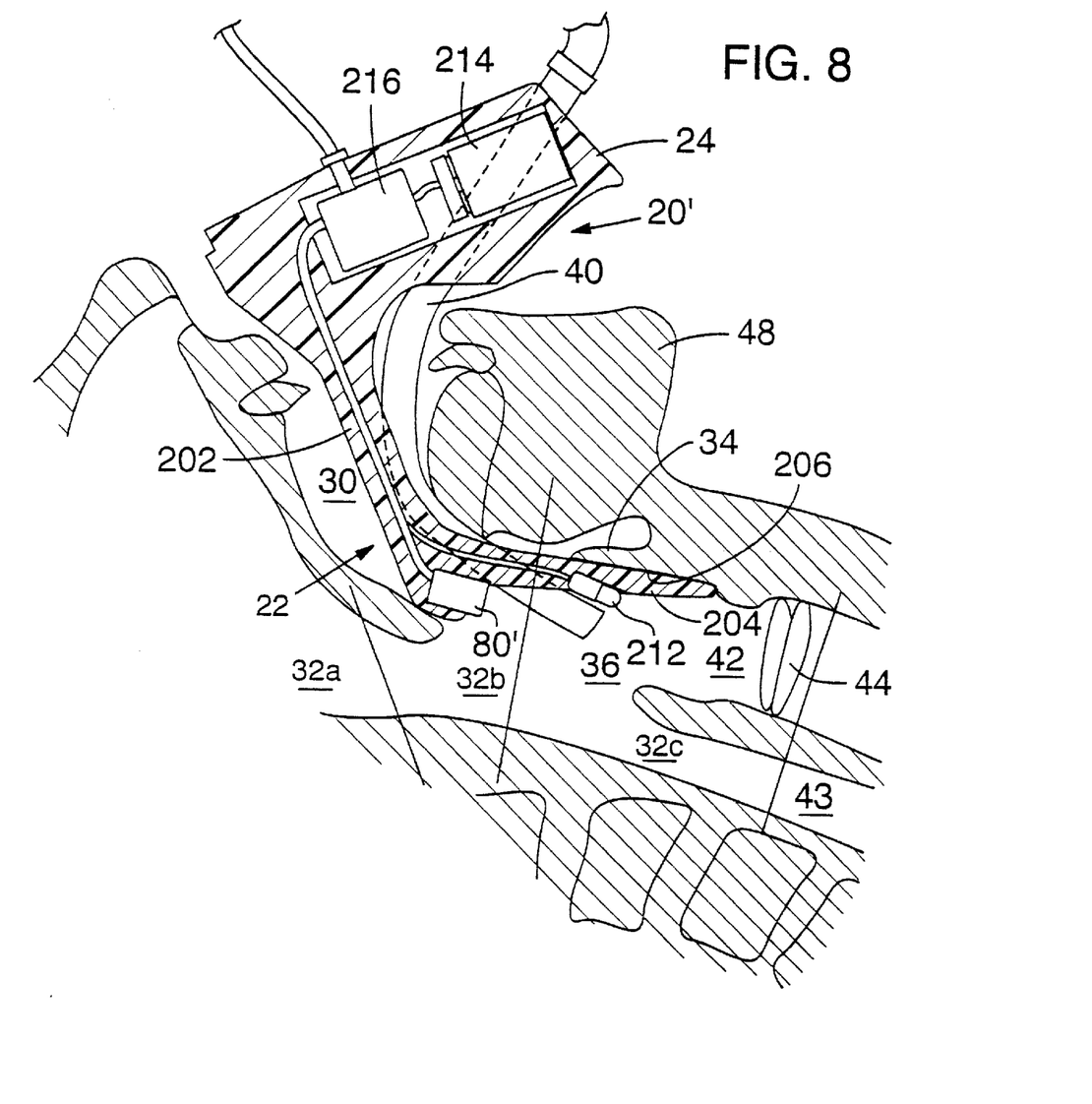
FIG. 8 is a side, elevation view of the instrument of FIG. 7 shown inserted into the mouth of a patient.
Figure 11A:
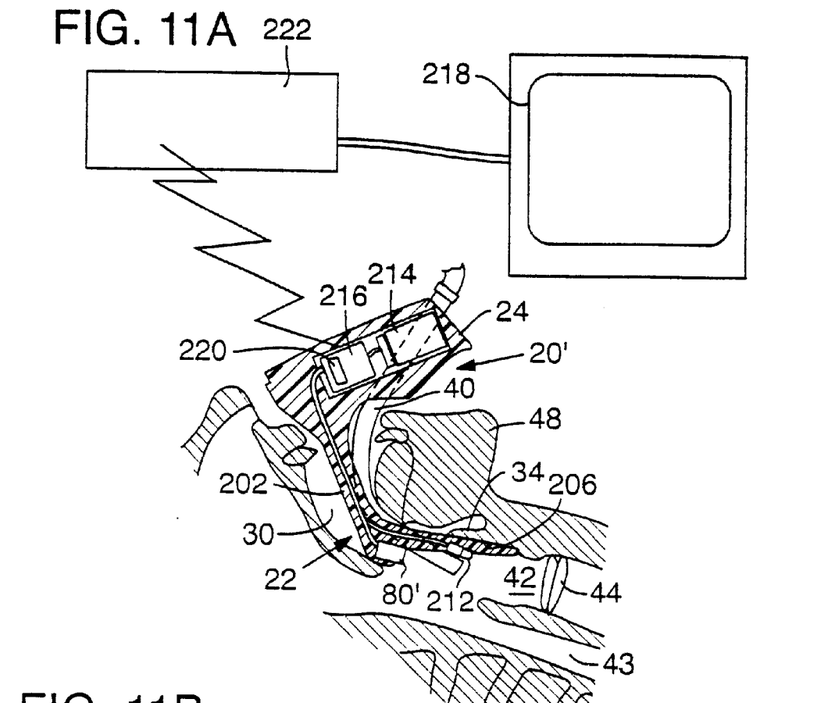
FIG. 11A is a block diagram of an exemplar viewing arrangement.
Figure 11B:
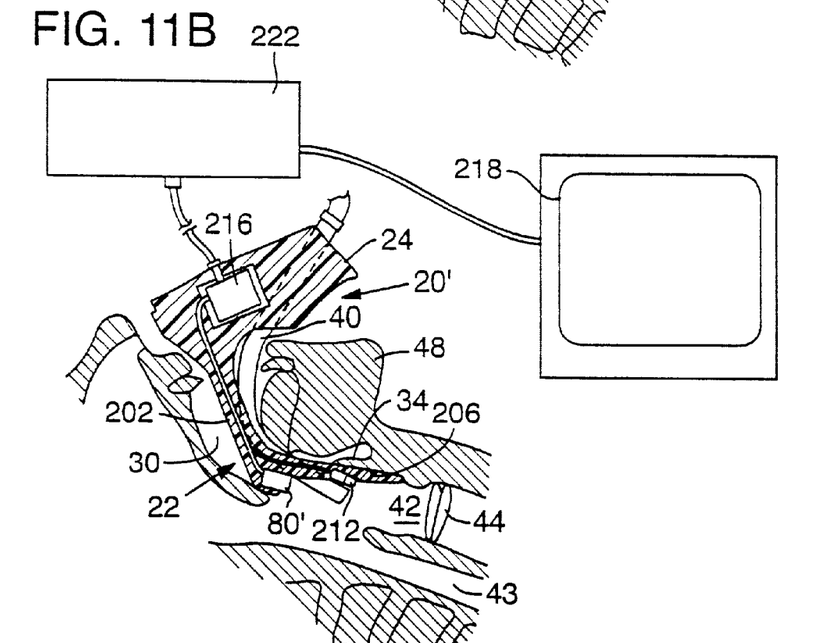
FIG. 11B is a block diagram of an alternative preferred exemplar viewing arrangement.

With particular reference to FIGS. 7, 8, and 11, a second preferred embodiment of an intubation instrument made and used in accord with the present invention includes a body 20' that generally comprises an elongated arm 22 with integrally attached handle 24, preferably integrally formed from metal or rigid plastic that can withstand sterilization. The arm includes an elongate base portion 202, and a lifter portion 204 extending therefrom as best shown in FIG. 7. The overall length of the arm is optimally sized to be positioned within a patient as previously described, and the lifter portion 204 is sized and shaped to have an elongate smooth surface 206 for engaging or lifting the patient's epiglottis 34 (FIG. 8), thereby to expose the glottis as best shown in FIG. 8. As a result, the epiglottis 34 and surrounding tissue are held by the instrument in a position where they do not occlude the glottis 36.

Preferably, the lifter portion 204 is at least approximately 3 centimeters long, and the angle 208 between the base portion 202 and lifter portion 204 is between 5° and 90°, inclusive. More preferably, the length 205 of the lifter portion 204 is between approximately 4 centimeters and 8 centimeters long, and the angle 208 between the lifter portion 204 and base portion 202 is between 30° and 60°. Even more preferably, the length 205 of the lifter portion 204 is approximately the same as the length 207 of the base portion 202, both of which are approximately 6 centimeters long, and the angle 208 between the lifter and base portions is approximately 45°. Obviously, the overall geometry between the base portion 202 and lifter portion 204 is important for effective operation of the instrument. Proportionately smaller sizes should be used for pediatric applications.

A viewing device, which is preferably a camera 80' operably secured to the instrument, is preferably positioned along the posterior surface of the lifter portion 204, near the transition portion between the base and lifter portions 202, 204, respectively, and aligned to provide a perspective view toward the distal end 210 of the lifter portion 204. More preferably, the camera 80' is mounted to the left side of the instrument when viewed from the handle 25, thereby permitting passage directly down the midline of the patient's tongue. The lifter portion 204 protects the camera from being blocked by tissue and debris. Moreover, positioning the camera 80' away from the distal end 210 of the lifter portion 204 provides the user with a clear perspective view of the entire area.

One or more lights, which are preferably Light Emitting Diodes 212 ("LED") are preferably positioned along the lifter portion to facilitate operator viewing. The use of one or more LED cold light elements in front of the camera lens provide needed light without producing any heat. Accordingly, unlike traditional expensive Zenon lights typically used on fiber optic laryngoscopes, economical LED lights will not burn sensitive membranes and will not damage the thin plastic cuff found on most endotracheal tubes.

The camera 80' is preferably a Complementary Metal Oxide Semiconductor. ("CMOS") or Charged Coupled Device ("CCD") hybrid camera, both of which are more compact, light weight, light sensitive, and economical, than traditional cameras used in such applications. Known manufacturers and sellers of such cameras include Sun Microsystems, Amain Electronics, and Misumi Electronics. Preferably, the camera 80' is operably connected to a power source 214, such as a battery or A/C connection, and suitable related electronics 216, which are stored in the handle 24 of the instrument. As best shown in FIGS. 11A&B, the camera 80' is operably connected to a display 218, either by a direct (FIG. 11B) or remote (FIG. 11A) connection. Such remote connections can include a transmitter 220 received within the instrument and the display 218 including a receiver 222 for receiving video signals from the transmitter 220. Alternatively, such a system can include infrared technology or the like. The camera 80' and related transmitter 220 can also communicate with a display, or other equipment such as remote locations via the evolving industry standard more commonly. known as "bluetooth." Such communication can also be used to transmit the information via the Internet or the like, thereby facilitating real-time remote incident analysis, advice, assistance, and/or teaching.

The display 218 may be detached from or attached to the instrument, and may also be configured to simultaneously display other relevant information such as the patient's vital signs and the like, thereby facilitating operator use of the instrument.

Preferably, the camera 80' is secured within a sealed chamber 224 within the arm 22, thereby protecting it from water, gasses, and chemicals used in sterilization procedures. More preferably, the chamber 224 contains nitrogen gas free from moisture, thereby avoiding undesirable condensation. Preferably, the CMOS or CCD camera body is also sealed.

A tightly fitted, transparent protective sheath (not shown) may be positioned over the assembly to facilitate cleaning and provide sterile multiple use of the device. The sheath is tightly fitted over the lens of the camera to prevent it from encumber the view. Preferably, the sheath is a transparent polymer, such as plastic, which sheds mucus and blood, has little tendency to fog during use, and equilibrates rapidly to airway temperature.

The instrument may also include paths (not shown) for transmitting oxygen and/or fluid to the camera lens, thereby assisting clearing and cleaning the lens during operation.

The embodiment can also include the guide path, groove and loop for slidably receiving an endotracheal tube 40 as with the first preferred embodiment. Alternatively, the instrument can be used as a conventional laryngoscope, without providing for receiving therein such an endotracheal tube 40.

It will be appreciated that the arrangement of the various components of the instrument presents an instrument that is substantially symmetrical about the long axis of the arm and handle. Thus the instrument is readily useable by a right- or left-handed operator.

C. Third Preferred Embodiment

With particular reference to FIGS. 9 and 10, a third preferred embodiment of an intubation instrument made and used in accord with the present invention is disclosed. It includes the body 20" that generally comprises an elongated arm 22 with integrally attached handle 24 of the second preferred embodiment, including the viewer and light. However, the lifter portion 204 of the arm 22 is pivotally secured to the base portion 202 at pivot point 301 as best shown in FIG. 9.

In particular, a locking mechanism 307, such as an actuation lever 300 having a handle 302 at one end extends through a channel 304 in the base portion 202 to pivot the lifter portion 204 about pivot point 301. Detents 306 between the actuation lever and base portion allow a user to select the desired angle 208 between the lifter portion 204 and base portion 202, and lock that position in place. Accordingly, by manipulating the actuation lever, the optimal angle 208 between the lifter portion 204 and base portion 202 for a particular patient may be selected on site by the practitioner.

This embodiment can also include the guide path, groove and loop for slidably receiving an endotracheal tube 40 as with the first preferred embodiment. Alternatively, and as shown in FIG. 9, the instrument can be. used as a conventional laryngoscope, without providing for receiving therein such a endotracheal tube 40.

D. Defogger Assembly

Figure 12:
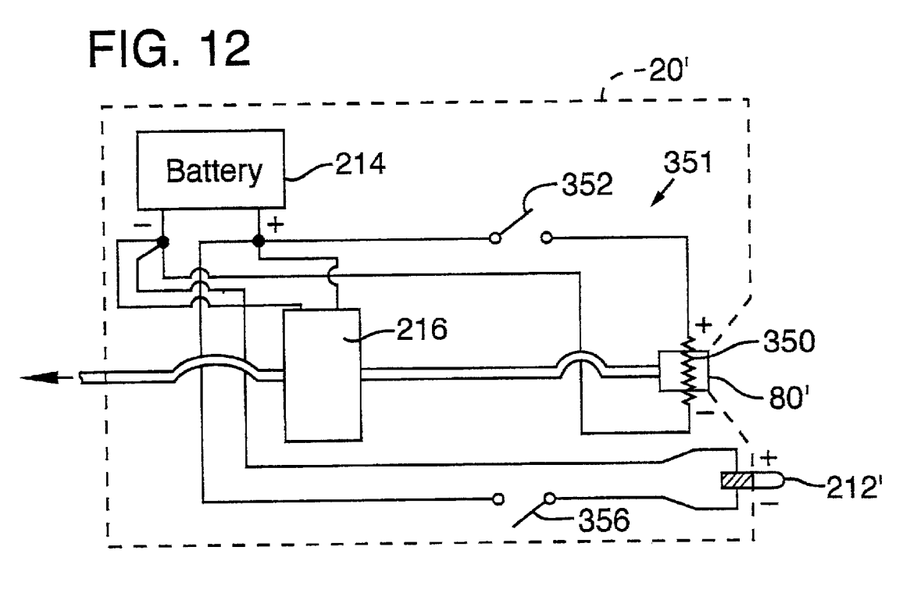
FIG. 12 is a schematic electrical diagram of a possible viewer defogging element assembly for use on the instrument.
Figure 13:
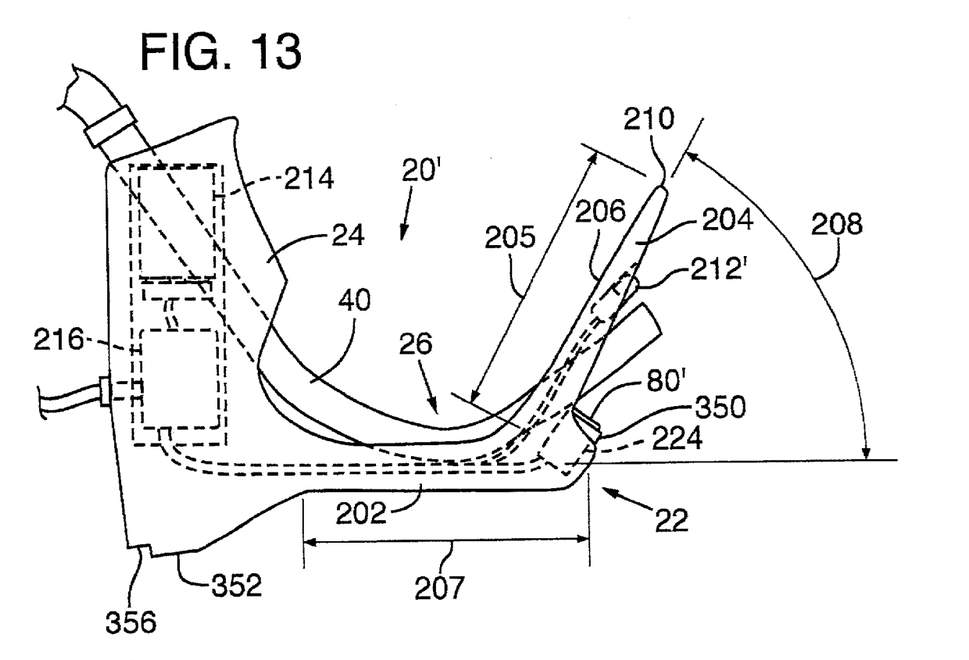
FIG. 13 is a side, elevation view of the instrument of FIG. 7 having a viewer defogging element assembly of FIG. 12 operably secured thereto.

Referring to FIGS. 12 and 13, a defogger assembly 351 that defogs the lense of the viewer on an instrument 20' by heating the lense is disclosed. One such structure for heating the lense includes thermally-coupling a heating element, such as a resistor 350 or coil, to the lense of the viewer. For example, the resistor 350 is preferably positioned adjacent to the lense and placed in electrical communication with a power source 214. Preferably, the components of the defogger assembly, such as the power source 214, heating element, and related wiring, are contained within the instrument 20', thereby maintaining the portability of the instrument 20'. More preferably, the power source 214 is a low voltage direct current battery or the like.

The resistor 350 and current are selected so as to heat the lense to a desired temperature to permit defogging, while still preventing the resistor from becoming hot enough to burn a patient or damage any components of the instrument. Preferably, the heating element is regulated so as to maintain an optimal temperature. For example, a thermostat operably secured to the defogger assembly can modulate current from the power source based on the level of detected temperature so as to prevent the heating element from becoming too hot.

Preferably, a switch 352 is operably secured to the resistor 350 such that power to the heating element may be turned on or off as needed to defog the lense of the viewer by heating the lense. The switch 352 may be manually controlled as shown in FIGS. 12 and 13, or controlled by internal electronics so as to activate under predetermined conditions. For example, in cases where the viewer is an electronically actuated camera, the internal electronics can power the heating element whenever the camera is activated. Alternatively, in cases where the instrument includes a light source 212', the defogger assembly 351 can be activated whenever the light source 212' is activated, for example, by activating light switch 356.

While the present invention has been described in terms of preferred embodiments, it will be appreciated by one of ordinary skill that the spirit and scope of the invention is not limited to those embodiments, but extend to the various modifications and equivalents as defined in the appended claims. For example, other types of viewers could be used. Moreover, additional channels could be provided for delivering other devices to the distal end of the instrument. FIG. 1 shows in dashed lines 110 such an alternative channel that would permit the advance of elongated forceps to the distal end of the instrument to be used, for example, in removing foreign objects from the larynx. Similarly, although the defogger assembly 351 is shown operably secured to the instrument 20' of the second preferred embodiment, it may be readily adapted to operate effectively on any of the disclosed instruments or their equivalents thereto.

What is claimed is:

1. An intubation instrument, a portion of which is for insertion into a patient through the patient's mouth, the patient having a respiratory system with an oropharynx, a laryngopharynx, and an epiglottis, said intubation instrument comprising:

a body having a handle attached thereto;

an elongate arm having an elongate base portion operably secured to said body at one end and an elongate lifter portion extending from said elongate base portion toward an opposite end of said elongate base portion thereby defining an angle between said elongate base portion and said elongate lifter portion, said elongate base portion having a first defined length, said first defined length being long enough to extend through the patient's mouth into the patient's oropharynx;

said elongate lifter portion having,
- a distal end for insertion distal-end first through a patient's mouth,
- a second defined length, said second defined length being long enough to extend into the laryngopharynx and operably engage the epiglottis of the patient when the elongate base portion is extended into the patient's oropharynx, and,
- a smooth surface for engaging the patient's epiglottis;

a viewer operably secured to said elongate arm and directed toward the distal end of said elongate lifter portion; and, a heating element in electrical communication with a power source and in thermal communication with the viewer so as to defog the viewer.

2. The intubation instrument of claim 1, wherein the viewer positioned substantially near where said elongate base portion meets said elongate lifter portion of the elongate arm.

3. The intubation instrument of claim 2, wherein said viewer is a telescope.

4. The intubation instrument of claim 2, wherein said viewer is a Complementary Metal Oxide Semiconductor camera.

5. The intubation instrument of claim 2, wherein said viewer is a Charged Coupled Device camera.

6. The intubation instrument of claim 1, wherein said heating element is a resistor.

7. The intubation instrument of claim 1, wherein said heating element and said power source are contained within the intubation instrument.

8. The intubation instrument of claim 1, wherein said power source is a low voltage, direct current battery.

9. The intubation instrument of claim 1, further including a switch in electrical communication with said heating element and said power source.

10. The intubation instrument of claim 9, wherein said switch is manually activated.

11. The intubation instrument of claim 9, wherein said switch is activated when said viewer is activated.

12. The intubation instrument of claim 9, further including a light operably secured to said elongate arm, and said switch is activated when said light is activated.

13. The intubation instrument of claim 9, wherein said switch is activated when said viewer is activated.

14. The intubation instrument of claim 1, further including a temperature regulator for regulating the temperature of said heating element.

15. The intubation instrument of claim 14, wherein said temperature regulator is a thermostat.

16. The intubation instrument of claim 1, wherein said heating element is positioned adjacent to said viewer.

17. An intubation instrument, a portion of which is for insertion into a patient through the patient's mouth, comprising:

a body having a handle attached thereto;

an elongate arm having an elongate base portion attached to the body and an elongate lifter portion extending from said elongate base portion, said elongate base portion having a first defined length, said elongate lifter portion having a second defined length and a smooth surface for engaging the patient's epiglottis and a distal end for insertion distal-end first through a patient's mouth, said elongate arm defining an anterior side positioned toward said handle and an opposite posterior side;

a viewer operably secured to said posterior side of said elongate arm directed toward the distal end of said elongate lifter portion; and, a heating element in electrical communication with a power source and in thermal communication with the viewer so as to defog the viewer.

18. The intubation instrument of claim 17, further including a switch in electrical communication with said heating element and said power source.

19. The intubation instrument of claim 18, wherein said switch is manually activated.

20. An intubation instrument, a portion of which is for insertion into a patient through the patient's mouth, comprising:

a body having a handle attached thereto;

an elongate arm having an elongate base portion operably secured to said body at one end and an elongate lifter portion extending from said elongate base portion toward an opposite end of said elongate base portion, said elongate lifter portion having a smooth surface for engaging the patient's epiglottis and a distal end for insertion distal-end first through a patient's mouth;

said elongate lifter portion being at least as long as said elongate base portion and extending from said elongate base portion by at least a 5 degree angle;

a viewer operably secured to said elongate arm directed toward the distal end of said elongate lifter portion; and, a heating element in electrical communication with a power source and in thermal communication with the viewer so as to defog the viewer.

* * * * *